(12) United States Patent
Kim et al.

(10) Patent No.: US 9,353,388 B2
(45) Date of Patent: May 31, 2016

(54) MICROORGANISM OVER-EXPRESSING LACTIC ACID TRANSPORTER GENE AND HAVING INHIBITORY PATHWAY OF LACTIC ACID DEGRADATION, AND METHOD OF PRODUCING LACTIC ACID USING THE MICROORGANISM

(71) Applicant: Samsung Electronics Co., Ltd., Suwon-si, Gyeonggi-do (KR)

(72) Inventors: Jae-young Kim, Suwon-si (KR); Jin-kyu Kang, Daegeon (KR); Chang-duk Kang, Gwacheon-si (KR); Sung-soo Kim, Hwaseong-si (KR); Jae-chan Park, Yongin-si (KR); Byung-jo Yu, Suwon-si (KR); Ju-young Lee, Daegu (KR); Hui-sub Lim, Seoul (KR)

(73) Assignee: SAMSUNG ELECTRONICS CO., LTD., Suwon-Si (KR)

( * ) Notice: Subject to any disclaimer, the term of this patent is extended or adjusted under 35 U.S.C. 154(b) by 0 days.

(21) Appl. No.: 14/173,543

(22) Filed: Feb. 5, 2014

(65) Prior Publication Data

US 2014/0220647 A1 Aug. 7, 2014

(30) Foreign Application Priority Data

Feb. 5, 2013 (KR) ........................ 10-2013-0012938

(51) Int. Cl.
*C12P 7/56* (2006.01)
*C12N 15/70* (2006.01)
*C12N 1/16* (2006.01)
*C07K 14/395* (2006.01)

(52) U.S. Cl.
CPC *C12P 7/56* (2013.01); *C07K 14/395* (2013.01)

(58) Field of Classification Search
CPC combination set(s) only.
See application file for complete search history.

(56) References Cited

U.S. PATENT DOCUMENTS

| | | | |
|---|---|---|---|
| 6,429,006 B1 * | 8/2002 | Porro et al. | 435/254.2 |
| 8,317,953 B2 * | 11/2012 | Sawka et al. | 149/109.6 |
| 2003/0032152 A1 | 2/2003 | Porro et al. | |
| 2011/0104769 A1 | 5/2011 | Porro et al. | |
| 2012/0064581 A1 | 3/2012 | Palsson et al. | |
| 2012/0129231 A1 | 5/2012 | Wang et al. | |

OTHER PUBLICATIONS

Branduardi et al., Lactate production yield from engineered yeasts is dependent from the host background, the lactate dehydrogenase source and the lactate export, *Microbial Cell Factories*, 5(4); 1-12 (2006).
Mansour et al., Lactate and Amino Acid Catabolism in the Cheese-Ripening Yeast *Yarrowa lipolytica*, *Applied and Environmental Microbiology*, 74(21): 6505-6512 (2008).
Ookubo et al., Improvement of L-Lactate Production by CYB2 Gene Disruption in a Recombinant *Saccharomyces cerevisiae* Strain under Low pH Condition, Bioscience Biotechnology Biochemistry, 72(11): 3063-3066 (2008).
Pacheco et al., Lactic acid production in *Saccharomyces cerevisiae* is modulated by expression of the monocarboxylate transporters Jen1 and Ady2, *FEMS Yeast Research*, 12: 375-381 (2012).

* cited by examiner

*Primary Examiner* — Kagnew H Gebreyesus
(74) *Attorney, Agent, or Firm* — Leydig, Voit & Mayer, Ltd.

(57) ABSTRACT

A recombinant microorganism comprising a lactic acid (LA) transporter, wherein the expression of the LA transporter in the recombinant microorganism is increased relative to a parent microorganism, and a method of producing lactic acid using same.

11 Claims, 4 Drawing Sheets

SEQUENCE LISTING

<160> NUMBER OF SEQ ID NOS: 7

<210> SEQ ID NO 1
<211> LENGTH: 616
<212> TYPE: PRT
<213> ORGANISM: Saccharomyces cerevisiae

<400> SEQUENCE: 1

```
Met Ser Ser Ser Ile Thr Asp Glu Lys Ile Ser Gly Glu Gln Gln Gln
1               5                   10                  15

Pro Ala Gly Arg Lys Leu Tyr Tyr Asn Thr Ser Thr Phe Ala Glu Pro
            20                  25                  30

Pro Leu Val Asp Gly Glu Gly Asn Pro Ile Asn Tyr Glu Pro Glu Val
        35                  40                  45

Tyr Asn Pro Asp His Glu Lys Leu Tyr His Asn Pro Ser Leu Pro Ala
    50                  55                  60

Gln Ser Ile Gln Asp Thr Arg Asp Asp Glu Leu Leu Glu Arg Val Tyr
65                  70                  75                  80

Ser Gln Asp Gln Gly Val Glu Tyr Glu Glu Asp Glu Glu Asp Lys Pro
                85                  90                  95

Asn Leu Ser Ala Ala Ser Ile Lys Ser Tyr Ala Leu Thr Arg Phe Thr
            100                 105                 110

Ser Leu Leu His Ile His Glu Phe Ser Trp Glu Asn Val Asn Pro Ile
        115                 120                 125

Pro Glu Leu Arg Lys Met Thr Trp Gln Asn Trp Asn Tyr Phe Phe Met
    130                 135                 140

Gly Tyr Phe Ala Trp Leu Ser Ala Ala Trp Ala Phe Phe Cys Val Ser
145                 150                 155                 160

Val Ser Val Ala Pro Leu Ala Glu Leu Tyr Asp Arg Pro Thr Lys Asp
                165                 170                 175

Ile Thr Trp Gly Leu Gly Leu Val Leu Phe Val Arg Ser Ala Gly Ala
            180                 185                 190

Val Ile Phe Gly Leu Trp Thr Asp Lys Ser Ser Arg Lys Trp Pro Tyr
        195                 200                 205

Ile Thr Cys Leu Phe Leu Phe Val Ile Ala Gln Leu Cys Thr Pro Trp
    210                 215                 220

Cys Asp Thr Tyr Glu Lys Phe Leu Gly Val Arg Trp Ile Thr Gly Ile
225                 230                 235                 240

Ala Met Gly Gly Ile Tyr Gly Cys Ala Ser Ala Thr Ala Ile Glu Asp
                245                 250                 255

Ala Pro Val Lys Ala Arg Ser Phe Leu Ser Gly Leu Phe Phe Ser Ala
            260                 265                 270

Tyr Ala Met Gly Phe Ile Phe Ala Ile Ile Phe Tyr Arg Ala Phe Gly
        275                 280                 285

Tyr Phe Arg Asp Asp Gly Trp Lys Ile Leu Phe Trp Phe Ser Ile Phe
    290                 295                 300

Leu Pro Ile Leu Leu Ile Phe Trp Arg Leu Leu Trp Pro Glu Thr Lys
305                 310                 315                 320

Tyr Phe Thr Lys Val Leu Lys Ala Arg Lys Leu Ile Leu Ser Asp Ala
                325                 330                 335

Val Lys Ala Asn Gly Gly Glu Pro Leu Pro Lys Ala Asn Phe Lys Gln
```

340             345                 350
Lys Met Val Ser Met Lys Arg Thr Val Gln Lys Tyr Trp Leu Leu Phe
            355                 360                 365
Ala Tyr Leu Val Val Leu Leu Val Gly Pro Asn Tyr Leu Thr His Ala
        370                 375                 380
Ser Gln Asp Leu Leu Pro Thr Met Leu Arg Ala Gln Leu Gly Leu Ser
385                 390                 395                 400
Lys Asp Ala Val Thr Val Ile Val Val Thr Asn Ile Gly Ala Ile
                405                 410                 415
Cys Gly Gly Met Ile Phe Gly Gln Phe Met Glu Val Thr Gly Arg Arg
            420                 425                 430
Leu Gly Leu Leu Ile Ala Cys Thr Met Gly Gly Cys Phe Thr Tyr Pro
                435                 440                 445
Ala Phe Met Leu Arg Ser Glu Lys Ala Ile Leu Gly Ala Gly Phe Met
            450                 455                 460
Leu Tyr Phe Cys Val Phe Gly Val Trp Gly Ile Leu Pro Ile His Leu
465                 470                 475                 480
Ala Glu Leu Ala Pro Ala Asp Ala Arg Ala Leu Val Ala Gly Leu Ser
                485                 490                 495
Tyr Gln Leu Gly Asn Leu Ala Ser Ala Ala Ser Thr Ile Glu Thr
            500                 505                 510
Gln Leu Ala Asp Arg Tyr Pro Leu Glu Arg Asp Ala Ser Gly Ala Val
            515                 520                 525
Ile Lys Glu Asp Tyr Ala Lys Val Met Ala Ile Leu Thr Gly Ser Val
        530                 535                 540
Phe Ile Phe Thr Phe Ala Cys Val Phe Val Gly His Glu Lys Phe His
545                 550                 555                 560
Arg Asp Leu Ser Ser Pro Val Met Lys Lys Tyr Ile Asn Gln Val Glu
                565                 570                 575
Glu Tyr Glu Ala Asp Gly Leu Ser Ile Ser Asp Ile Val Glu Gln Lys
            580                 585                 590
Thr Glu Cys Ala Ser Val Lys Met Ile Asp Ser Asn Val Ser Lys Thr
            595                 600                 605
Tyr Glu Glu His Ile Glu Thr Val
        610                 615

<210> SEQ ID NO 2
<211> LENGTH: 1851
<212> TYPE: DNA
<213> ORGANISM: Saccharomyces cerevisiae

<400> SEQUENCE: 2

```
atgtcgtcgt caattacaga tgagaaaata tctggtgaac agcaacaacc tgctggcaga      60
aaactatact ataacacaag tacatttgca gagcctcctc tagtggacgg agaaggtaac     120
cctataaatt atgagccgga agtttacaac ccggatcacg aaaagctata ccataaccca     180
tcactgcctg cacaatcaat tcaggataca agagatgatg aattgctgga aagagtttat     240
agccaggatc aaggtgtaga gtatgaggaa gatgaagagg ataagccaaa cctaagcgct     300
gcgtccatta aagttatgc tttaacgaga tttacgtcct tactgcacat ccacgagttt     360
tcttgggaga atgtcaatcc catacccgaa ctgcgcaaaa tgacatggca gaattggaac     420
tatttttta tgggttattt tgcgtggttg tctgcggctt gggccttctt ttgcgtttca     480
gtatcagtcg ctccattggc tgaactatat gacagaccaa ccaaggacat cacctggggg     540
```

```
ttgggattgg tgttatttgt tcgttcagca ggtgctgtca tatttggttt atggacagat    600
aagtcttcca gaaagtggcc gtacattaca tgtttgttct tatttgtcat tgcacaactc    660
tgtactccat ggtgtgacac atacgagaaa tttctgggcg taaggtggat aaccggtatt    720
gctatgggag gaatttacgg atgtgcttct gcaacagcga ttgaagatgc acctgtgaaa    780
gcacgttcgt tcctatcagg tctattttt tctgcttacg ctatggggtt catatttgct    840
atcattttt acagagcctt tggctacttt agggatgatg ctggaaaat attgttttgg    900
tttagtattt ttctaccaat tctactaatt ttctggagat tgttatggcc tgaaacgaaa    960
tacttcacca aggttttgaa agcccgtaaa ttaatattga gtgacgcagt gaaagctaat   1020
ggtggcgagc ctctaccaaa agccaacttt aaacaaaaga tggtatccat gaagagaaca   1080
gttcaaaagt actggttgtt gttcgcatat ttggttgttt tattggtggg tccaaattac   1140
ttgactcatg cttctcaaga cttgttgcca accatgctgc gtgcccaatt aggcctatcc   1200
aaggatgctg tcactgtcat tgtagtggtt accaacatcg gtgctatttg tgggggtatg   1260
atatttggac agttcatgga agttactgga agaagattag gcctattgat tgcatgcaca   1320
atgggtggtt gcttcaccta ccctgcattt atgttgagaa gcgaaaaggc tatattaggt   1380
gccggtttca tgttatattt ttgtgtcttt ggtgtctggg gtatcctgcc cattcacctt   1440
gcagagttgg cccctgctga tgcaagggct ttggttgccg gtttatctta ccagctaggt   1500
aatctagctt ctgcagcggc ttccacgatt gagacacagt tagctgatag atacccatta   1560
gaaagagatg cctctggtgc tgtgattaaa gaagattatg ccaaagttat ggctatcttg   1620
actggttctg ttttcatctt cacatttgct tgtgttttg ttggccatga gaaattccat   1680
cgtgatttgt cctctcctgt tatgaagaaa tatataaacc aagtggaaga atacgaagcc   1740
gatggtcttt cgattagtga cattgttgaa caaaagacgg aatgtgcttc agtgaagatg   1800
attgattcga acgtctcaaa gacatatgag gagcatattg agaccgttta a           1851
```

<210> SEQ ID NO 3
<211> LENGTH: 283
<212> TYPE: PRT
<213> ORGANISM: Saccharomyces cerevisiae

<400> SEQUENCE: 3

```
Met Ser Asp Lys Glu Gln Thr Ser Gly Asn Thr Asp Leu Glu Asn Ala
1               5                   10                  15

Pro Ala Gly Tyr Tyr Ser Ser His Asp Asn Asp Val Asn Gly Val Ala
            20                  25                  30

Glu Asp Glu Arg Pro Ser His Asp Ser Leu Gly Lys Ile Tyr Thr Gly
        35                  40                  45

Gly Asp Asn Asn Glu Tyr Ile Tyr Ile Gly Arg Gln Lys Phe Leu Lys
    50                  55                  60

Ser Asp Leu Tyr Gln Ala Phe Gly Gly Thr Leu Asn Pro Gly Leu Ala
65                  70                  75                  80

Pro Ala Pro Val His Lys Phe Ala Asn Pro Ala Leu Gly Leu Ser
            85                  90                  95

Ala Phe Ala Leu Thr Thr Phe Val Leu Ser Met Phe Asn Ala Arg Ala
            100                 105                 110

Gln Gly Ile Thr Val Pro Asn Val Val Gly Cys Ala Met Phe Tyr
        115                 120                 125

Gly Gly Leu Val Gln Leu Ile Ala Gly Ile Trp Glu Ile Ala Leu Glu
    130                 135                 140
```

Asn Thr Phe Gly Gly Thr Ala Leu Cys Ser Tyr Gly Gly Phe Trp Leu
145                 150                 155                 160

Ser Phe Ala Ala Ile Tyr Ile Pro Trp Phe Gly Ile Leu Glu Ala Tyr
                165                 170                 175

Glu Asp Asn Glu Ser Asp Leu Asn Asn Ala Leu Gly Phe Tyr Leu Leu
            180                 185                 190

Gly Trp Ala Ile Phe Thr Phe Gly Leu Thr Val Cys Thr Met Lys Ser
        195                 200                 205

Thr Val Met Phe Phe Leu Leu Phe Phe Leu Leu Ala Leu Thr Phe Leu
    210                 215                 220

Leu Leu Ser Ile Gly His Phe Ala Asn Arg Leu Gly Val Thr Arg Ala
225                 230                 235                 240

Gly Gly Val Leu Gly Val Val Ala Phe Ile Ala Trp Tyr Asn Ala
                245                 250                 255

Tyr Ala Gly Val Ala Thr Lys Gln Asn Ser Tyr Val Leu Ala Arg Pro
                260                 265                 270

Phe Pro Leu Pro Ser Thr Glu Arg Val Ile Phe
            275                 280

<210> SEQ ID NO 4
<211> LENGTH: 852
<212> TYPE: DNA
<213> ORGANISM: Saccharomyces cerevisiae

<400> SEQUENCE: 4

```
atgtctgaca aggaacaaac gagcggaaac acagatttgg agaatgcacc agcaggatac      60
tatagttccc atgataacga cgttaatggc gttgcagaag atgaacgtcc atctcatgat     120
tcgttgggca agatttacac tggaggtgat aacaatgaat atatctatat tgggcgtcaa     180
aagttttga agagcgactt ataccaagcc tttggtggta ccttgaatcc agggttagct     240
cctgctccag tgcacaaatt tgctaatcct gcgcccttag tctttcagc cttcgcgttg     300
acgacatttg tgctgtccat gttcaatgcg agagcgcaag ggatcactgt tcctaatgtt     360
gtcgtcggtt gtgctatgtt ttatggtggt ttggtgcaat tgattgctgg tatttgggag     420
atagctttgg aaaatacttt tggtggtacc gcattatgtt cttacggtgg ttttggttg     480
agtttcgctg caatttacat tccttggttt ggtatcttgg aagcttacga agacaatgaa     540
tctgatttga ataatgcttt aggatttat ttgttgggt gggccatctt tacgtttggt     600
ttaaccgttt gtaccatgaa atccactgtt atgttctttt tgttgttctt cttactagca     660
ttaactttcc tactgttgtc tattggtcac tttgctaata gacttggtgt cacaagagct     720
ggtggtgtcc tgggagttgt tgttgctttc attgcttggt acaacgcata tgcaggtgtt     780
gctacaaagc agaattcata tgtactggct cgtccattcc cattaccatc tactgaaagg     840
gtaatctttt aa                                                         852
```

<210> SEQ ID NO 5
<211> LENGTH: 1776
<212> TYPE: DNA
<213> ORGANISM: Saccharomyces cerevisiae

<400> SEQUENCE: 5

```
atgctaaaat acaaaccttt actaaaaatc tcgaagaact gtgaggctgc tatcctcaga      60
gcgtctaaga ctagattgaa cacaatccgc gcgtacggtt ctaccgttcc aaaatccaag    120
tcgttcgaac aagactcaag aaaacgcaca cagtcatgga ctgccttgag agtcggtgca    180
```

```
attctagccg ctactagttc cgtggcgtat ctaaactggc ataatggcca aatagacaac    240
gagccgaaac tggatatgaa taaacaaaag atttcgcccg ctgaagttgc caagcataac    300
aagcccgatg attgttgggt tgtgatcaat ggttacgtat acgacttaac gcgattccta    360
ccaaatcatc caggtgggca ggatgttatc aagtttaacg ccgggaaaga tgtcactgct    420 attttttgaac cactacatgc tcctaatgtc atcgataagt atatagctcc cgagaaaaaa    480
ttgggtcccc ttcaaggatc catgcctcct gaacttgtct gtcctcctta tgctcctggt    540
gaaactaagg aagatatcgc tagaaaagaa caactaaaat cgctgctacc tcctctagat    600
aatattatta acctttacga cttttgaatac ttggcctctc aaactttgac taaacaagcg    660
tgggcctact attcctccgg tgctaacgac gaagttactc acagagaaaa ccataatgct    720
tatcatagga ttttttttcaa accaaagatc cttgtagatg tacgcaaagt agacatttca    780
actgacatgt tgggttctca tgtggatgtt cccttctacg tgtctgctac agctttgtgt    840
aaactgggaa acccccttaga aggtgaaaaa gatgtcgcca gaggttgtgg ccaaggtgtg    900
acaaaagtcc cacaaatgat atctactttg gcttcatgtt cccctgagga aattattgaa    960
gcagcaccct ctgataaaca aattcaatgg taccaactat atgttaactc tgatagaaag   1020
atcactgatg atttggttaa aaatgtagaa aagctgggtg taaaggcatt atttgtcact   1080
gtggatgctc caagtttagg tcaaagagaa aaagatatga agctgaaatt ttccaataca   1140
aaggctggtc caaaagcgat gaagaaaact aatgtagaag aatctcaagg tgcttcgaga   1200
gcgttatcaa agtttattga ccccctctttg acttggaaag atatagaaga gttgaagaaa   1260
aagacaaaac tacctattgt tatcaaaggt gttcaacgta ccgaagatgt tatcaaagca   1320
gcagaaatcg tgtaagtgg ggtggttcta tccaatcatg gtggtagaca attagatttt   1380
tcaagggctc ccattgaagt cctggctgaa accatgccaa tcctggaaca acgtaacttg   1440
aaggataagt tggaagtttt cgtggacggt ggtgttcgtc gtggtacaga tgtcttgaaa   1500
gcgttatgtc taggtgctaa aggtgttggt ttgggtagac cattcttgta tgcgaactca   1560
tgctatggtc gtaatggtgt tgaaaaagcc attgaaattt taagagatga aattgaaatg   1620
tctatgagac tattaggtgt tactagcatt gcggaattga gcctgatct tttagatcta   1680 tcaacactaa aggcaagaac agttggagta ccaaacgacg tgctgtataa tgaagtttat   1740
gagggaccta ctttaacaga atttgaggat gcatga                              1776
```

<210> SEQ ID NO 6
<211> LENGTH: 332
<212> TYPE: PRT
<213> ORGANISM: Rattus norvegicus

<400> SEQUENCE: 6

```
Met Ala Ala Leu Lys Asp Gln Leu Ile Val Asn Leu Leu Lys Glu Glu
1               5                   10                  15

Gln Val Pro Gln Asn Lys Ile Thr Val Val Gly Val Gly Ala Val Gly
                20                  25                  30

Met Ala Cys Ala Ile Ser Ile Leu Met Lys Asp Leu Ala Asp Glu Leu
            35                  40                  45

Ala Leu Val Asp Val Ile Glu Asp Lys Leu Lys Gly Glu Met Met Asp
        50                  55                  60

Leu Gln His Gly Ser Leu Phe Leu Lys Thr Pro Lys Ile Val Ser Ser
65                  70                  75                  80

Lys Asp Tyr Ser Val Thr Ala Asn Ser Lys Leu Val Ile Ile Thr Ala
                85                  90                  95
```

-continued

Gly Ala Arg Gln Gln Glu Gly Glu Ser Arg Leu Asn Leu Val Gln Arg
            100                 105                 110

Asn Val Asn Ile Phe Lys Phe Ile Ile Pro Asn Val Val Lys Tyr Ser
        115                 120                 125

Pro Gln Cys Lys Leu Leu Ile Val Ser Asn Pro Val Asp Ile Leu Thr
    130                 135                 140

Tyr Val Ala Trp Lys Ile Ser Gly Phe Pro Lys Asn Arg Val Ile Gly
145                 150                 155                 160

Ser Gly Cys Asn Leu Asp Ser Ala Arg Phe Arg Tyr Leu Met Gly Glu
                165                 170                 175

Arg Leu Gly Val His Pro Leu Ser Cys His Gly Trp Val Leu Gly Glu
            180                 185                 190

His Gly Asp Ser Ser Val Pro Val Trp Ser Gly Val Asn Val Ala Gly
                195                 200                 205

Val Ser Leu Lys Ser Leu Asn Pro Gln Leu Gly Thr Asp Ala Asp Lys
    210                 215                 220

Glu Gln Trp Lys Asp Val His Lys Gln Val Val Asp Ser Ala Tyr Glu
225                 230                 235                 240

Val Ile Lys Leu Lys Gly Tyr Thr Ser Trp Ala Ile Gly Leu Ser Val
                245                 250                 255

Ala Asp Leu Ala Glu Ser Ile Met Lys Asn Leu Arg Arg Val His Pro
            260                 265                 270

Ile Ser Thr Met Ile Lys Gly Leu Tyr Gly Ile Lys Glu Asp Val Phe
        275                 280                 285

Leu Ser Val Pro Cys Ile Leu Gly Gln Asn Gly Ile Ser Asp Val Val
    290                 295                 300

Lys Val Thr Leu Thr Pro Asp Glu Glu Ala Arg Leu Lys Lys Ser Ala
305                 310                 315                 320

Asp Thr Leu Trp Gly Ile Gln Lys Glu Leu Gln Phe
                325                 330

<210> SEQ ID NO 7
<211> LENGTH: 999
<212> TYPE: DNA
<213> ORGANISM: Rattus norvegicus

<400> SEQUENCE: 7
atggcagccc tcaaggacca gctgattgtg aatcttctta aggaagaaca ggtcccccag      60
aacaagatta cagttgttgg ggttggtgct gttggcatgg cttgtgccat cagtatctta     120
atgaaggact ggctgatga gcttgccctt gttgatgtca tagaagataa gctaaaggga     180
gagatgatgg atcttcagca tggcagcctt tccttaaga caccaaaaat tgtctccagc     240
aaagattata gtgtgactgc aaactccaag ctggtcatta tcaccgcggg ggcccgtcag     300
caagagggag agagccggct caatttggtc agcgaaacg tgaacatctt caagttcatc     360
attccaaatg ttgtgaaata cagtccacag tgcaaactgc tcatcgtctc aaacccagtg     420
gatatcttga cctacgtggc ttggaagatc agcggcttcc ccaaaaacag agttattgga     480
agtggttgca atctggattc ggctcggttc cgttacctga tgggagaaag gctgggagtt     540
catccactga gctgtcacgg gtgggtcctg ggagagcatg gcgactccag tgtgcctgtg     600
tggagtggtg tgaatgtcgc cggcgtctcc ctgaagtctc tgaacccgca gctgggcacg     660
gatgcagaca ggagcagtg gaaggatgtg cacaagcagg tggttgacag tgcatacgaa     720
gtgatcaagc tgaaaggtta cacatcctgg gccattggcc tctccgtggc agacttggcc     780

```
gagagcataa tgaagaacct taggcgggtg catcccattt ccaccatgat taagggtctc       840
tatggaatca aggaggatgt cttcctcagc gtcccatgta tcctgggaca aaatggaatc       900
tcagatgttg tgaaggtgac actgactcct gacgaggagg cccgcctgaa gaagagtgca       960 gatacctct ggggaatcca gaaggagctg cagttctaa                               999
```

MICROORGANISM OVER-EXPRESSING LACTIC ACID TRANSPORTER GENE AND HAVING INHIBITORY PATHWAY OF LACTIC ACID DEGRADATION, AND METHOD OF PRODUCING LACTIC ACID USING THE MICROORGANISM

CROSS-REFERENCE TO RELATED APPLICATION

This application claims the benefit of Korean Patent Application No. 10-2013-0012938, filed on 5 Feb. 2013, in the Korean Intellectual Property Office, the entire disclosure of which is hereby incorporated by reference.

INCORPORATION-BY-REFERENCE OF MATERIAL SUBMITTED ELECTRONICALLY

Incorporated by reference in its entirety herein is a computer-readable nucleotide/amino acid sequence listing submitted concurrently herewith and identified as follows: One 18,685 Byte ASCII (Text) file named "713569_ST25.TXT," created on Feb. 5, 2014.

BACKGROUND

1. Field

The present disclosure relates to recombinant microorganisms with improved lactate production, and methods of producing lactic acid using the same.

2. Description of the Related Art

Lactic acid (also referred to as lactate) is being widely used in a variety of industries such as food, pharmaceutical, chemical, and electronic fields. Lactic acid is a colorless, odorless, and low-volatile substance that is easily soluble in water. Lactic acid that is not toxic to the human body is used as a flavoring agent, an acidifier, a preserving agent, or the like. Also, lactic acid is a raw material of biodegradable polylactic acid (PLA) that is an alternative environmentally friendly polymeric material.

Technically, PLA is a polyester-based resin that is obtained by conversion to lactide in the form of a dimer and then by ring-opening polymerization, and PLA is available in various processing forms such as film, sheet, fiber, injection, and the like. Therefore, there has recently been increasing demand for PLA as a bio-plastic that may widely replace existing general-purpose petrochemical plastics such as polyethylene (PE), polypropylene (PP), polyethylene terephthalate (PET), polystyrene (PS), or the like.

In addition, lactic acid has a hydroxyl group and a carboxyl group at the same time and, thus, it is very reactive. Accordingly, lactic acid may be readily converted to an industrially important compound such as lactic acid ester, acetaldehyde, propylene glycol, or the like. Thus, lactic acid is in the spotlight as an alternative next generation raw chemical material in the field of chemical industry, as well.

In terms of modern industry, lactic acid is produced by a process of petrochemical synthesis and biotechnological fermentation. The petrochemical synthesis is carried out by oxidizing ethylene derived from crude oil, obtaining lactonitrile through acetaldehyde by adding hydrogen cyanide thereto, distilling for purification, and hydrolyzing the reaction product using hydrochloric acid or sulfuric acid to produce lactic acid. The biotechnological fermentation is carried out by using a renewable carbohydrate such as starch, sucrose, maltose, glucose, fructose, and xylose, as a substrate to produce lactic acid.

When a substance that may be obtained by a general chemistry reaction formula in several steps is produced using microorganisms, the substance may be produced more efficiently. Here, the substance is produced more efficiently than in general chemical synthesis in terms of cost and time, and thus there have been many studies using microorganisms. However, microorganisms do not produce only certain metabolites and, if certain metabolites are produced excessively, microbial growth is rather inhibited or the metabolite is no longer produced. Instead, useless byproducts may be produced. Therefore, it is urgent to solve the above-described problems and develop a strain that efficiently produces lactic acid.

SUMMARY

Provided is a recombinant microorganism that highly expresses lactic acid (LA) transporters relative to a parent microorganism.

Provided is a microorganism that highly expresses one or more LA transporters and has an inhibitory pathway of LA degradation relative to a parent microorganism.

Provided are methods of producing LA by using the recombinant microorganisms.

Additional aspects will be set forth in part in the description which follows and, in part, will be apparent from the description, or may be learned by practice of the presented embodiments.

BRIEF DESCRIPTION OF THE DRAWINGS

These and/or other aspects will become apparent and more readily appreciated from the following description of the embodiments, taken in conjunction with the accompanying drawings of which.

DETAILED DESCRIPTION

Figure 1:
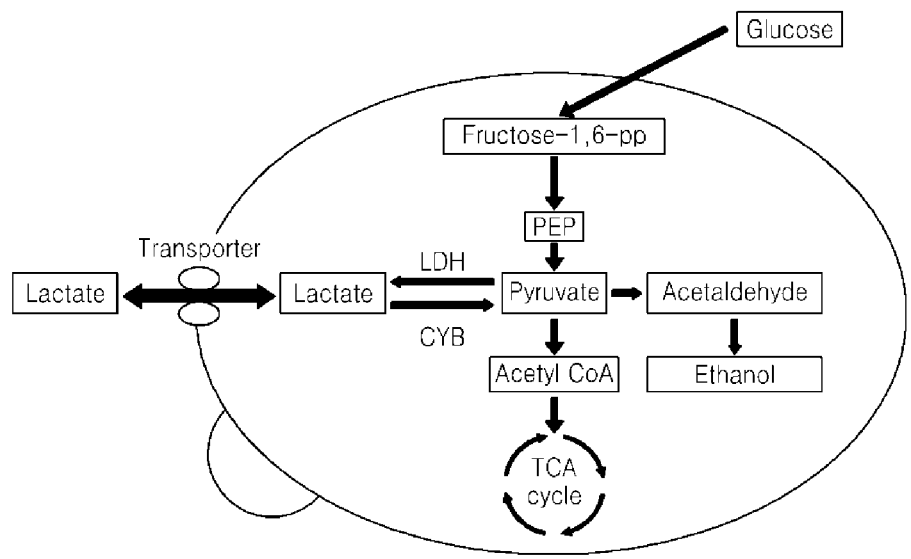
FIG. 1 is a diagram illustrating a pathway of lactic acid (LA) production.
Figure 2:
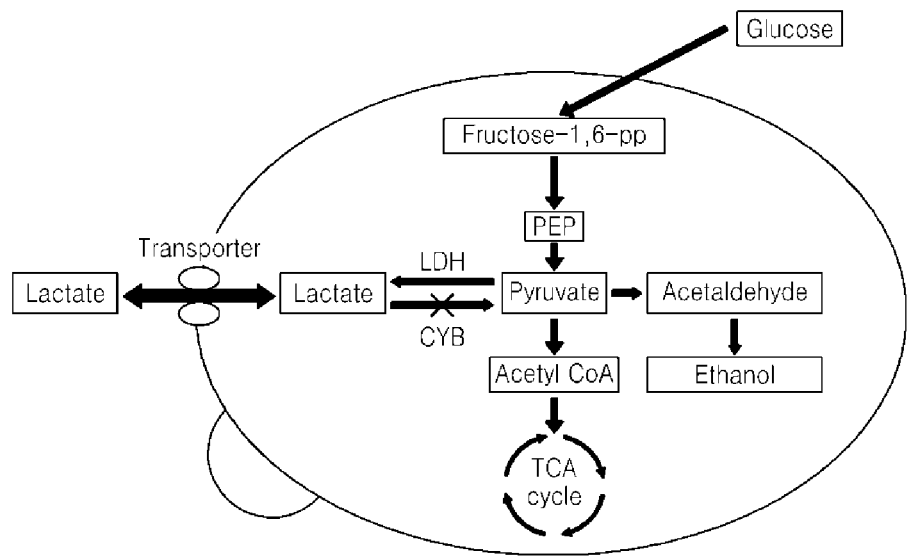
FIG. 2 is a diagram illustrating a transgenic pathway to increase a level of LA production.
Figure 3:
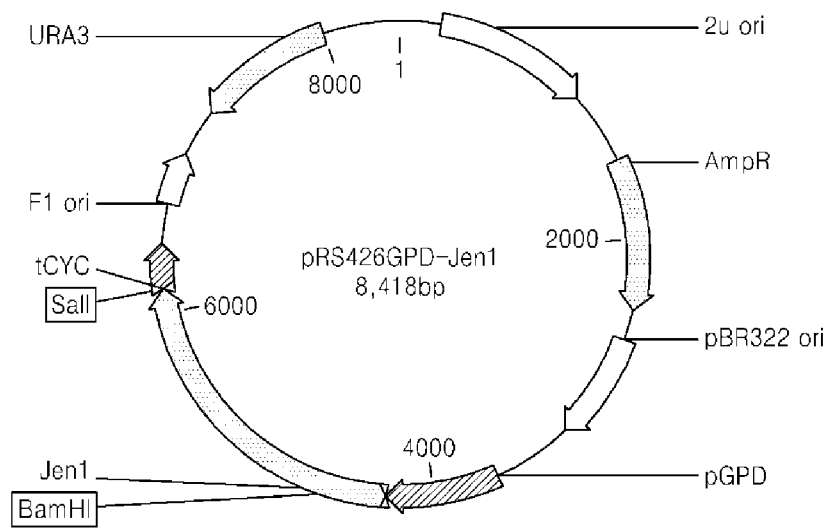
FIG. 3 is a diagram illustrating an LA transporter over-expression vector.
Figure 4:
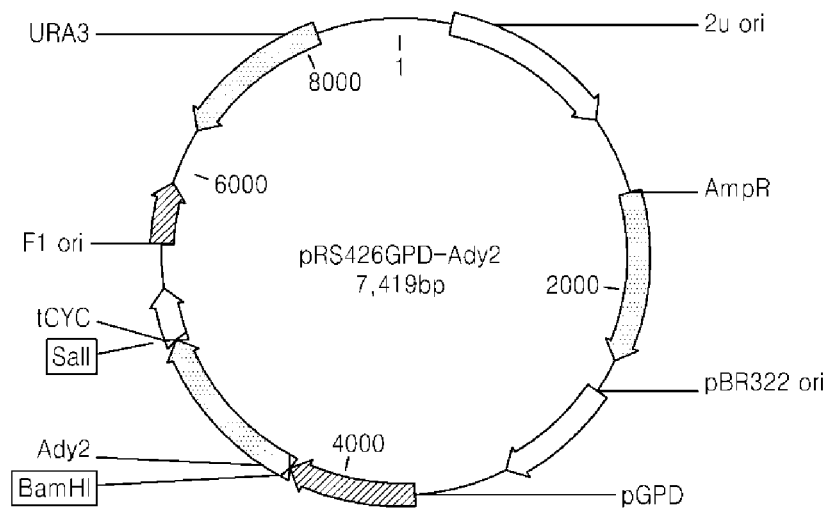
FIG. 4 is a diagram illustrating an LA transporter over-expression vector
Figure 5:
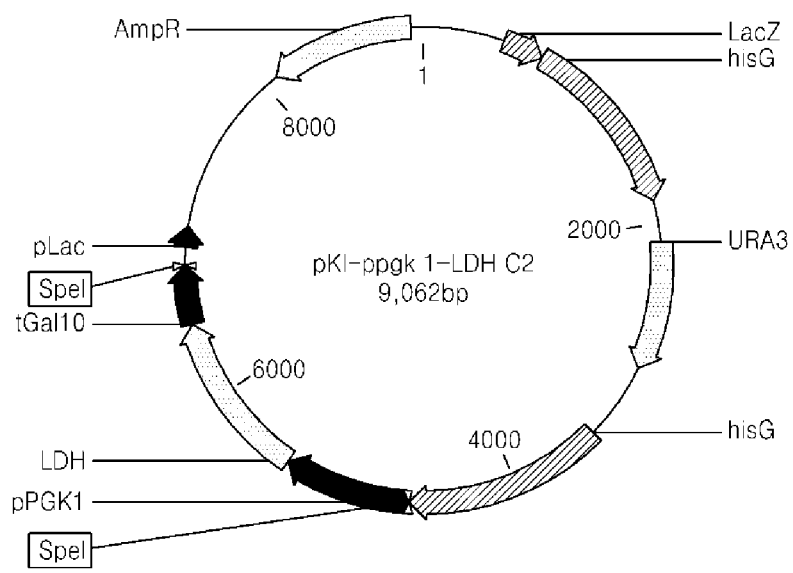
FIG. 5 is a diagram illustrating a template vector provided for LA gene deletion.
Figure 6:
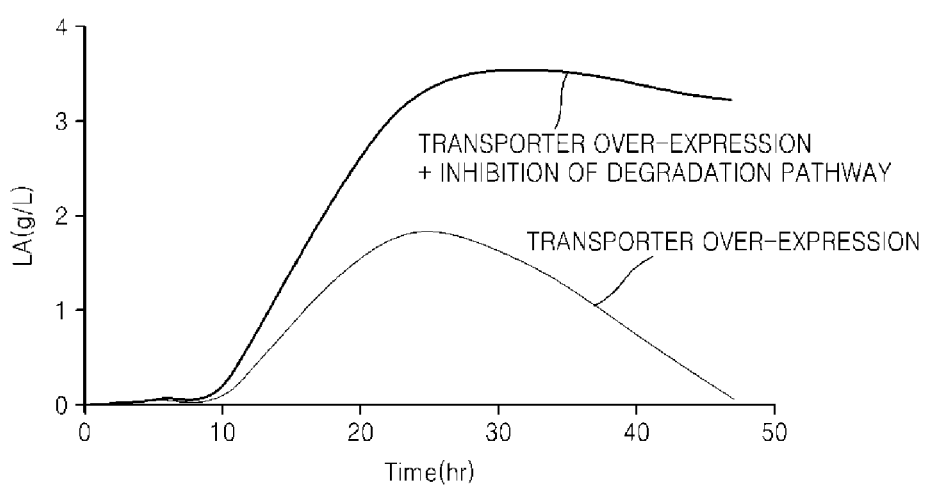
FIG. 6 is a graph illustrating LA output when a transporter is over-expressed or when a transporter is over-expressed and a pathway of LA degradation is inhibited. LA output (g/L) is indicated on the y-axis, and time (hours) is indicated on the x-axis.
Figure 7:
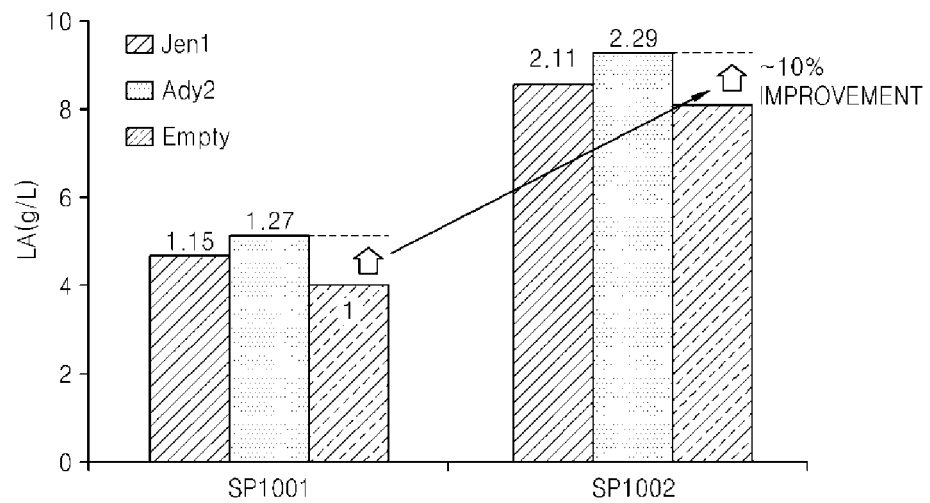
FIG. 7 is a graph illustrating LA output when a LA transporter (i.e., Jen1 or Ady2) is over-expressed in a strain with over-expressed lactate dehydrogenase (LDH). LA output (g/L) is indicated on the y-axis, and time (hours) is indicated on the x-axis. The SP1001 strain has a deletion in the pdc1 gene and over-expresses LDH. The SP1002 strain has deletions in the pdc1 gene (resulting in little or no pyruvate decarboxylase activity) and cyb2 gene (resulting in little or no lactate oxidoreductase activity) and over-expresses LDH.
Figure 8:
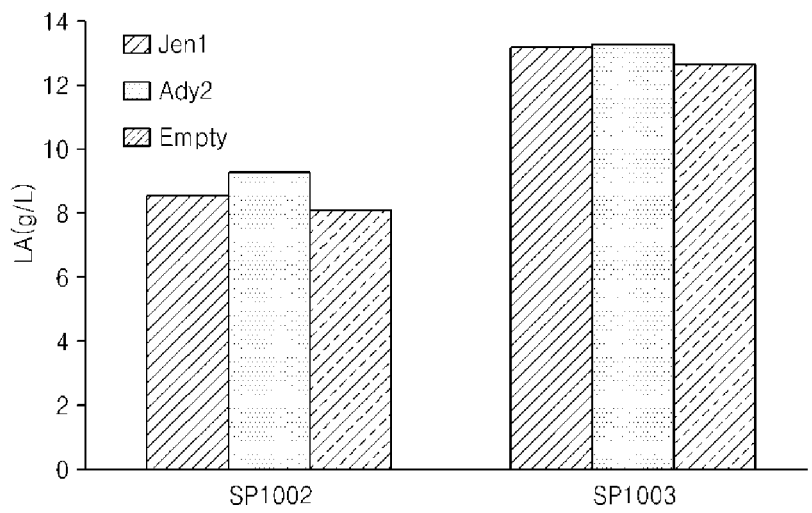
FIG. 8 is a graph illustrating LA output according to LDH expressions. As LDH gene is additionally introduced, the LA output is improved 1.5 times. LA output is indicated on the y-axis for the SP1002 and SP1003 strains. The SP1003 strain has deletions of the pdc 1 gene (resulting in little or no pyruvate decarboxylase activity) and cyb2 gene resulting in little or no lactate oxidoreductase activity) and insertion of two copies of the LDH, which leads to LDH over-expression.

According to an aspect of the present inventive concept, a recombinant microorganism that highly expresses a LA transporter is provided to prepare a recombinant microorganism that highly produces LA relative to a parent microorganism from which the recombinant microorganism was derived. The recombinant microorganism highly producing a LA transporter can produce a large amount of LA relative to a parent microorganism.

The recombinant microorganism may comprise a lactic acid (LA) transporter, wherein the expression of the LA transporter in the recombinant microorganism is increased relative to a parent microorganism. In addition, the LA transporter is expressed by expression of a lactic acid transporter gene in the recombinant microorganism. The lactic acid transporter gene may be introduced into the recombinant microorganism.

The above-described LA transporter may be Jen1 or Ady1. Jen1 may comprise, consist essentially of, and consist of the amino acid sequence of SEQ ID No: 1. Alternatively, an amino acid sequence of the LA transporter may have at least 80%, 85%, 90%, 95%, or 99% sequence identity with the amino acid sequence of SEQ ID NO: 1 as long as the LA transporter maintains its activity.

Ady2 may comprise, consist essentially of, or consist of the amino acid sequence of SEQ ID No: 3. Alternatively, an amino acid sequence of the LA transporter may have more than 80%, 85%, 90%, 95%, or 99% sequence identity with the amino acid sequence of SEQ ID NO: 3 as long as the LA transporter maintains its activity.

As used herein, "sequence identity" or "identity" in the context of two nucleic acid or polypeptide sequences includes reference to the residues in the two sequences which are the same when aligned for maximum correspondence over a specified comparison window. Means for making this adjustment are well-known to those of skill in the art. As used herein, "percentage of sequence identity" means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

In order to highly express the LA transporter in a cell, a nucleic acid (e.g., a gene) that encodes a LA transporter is introduced into the cell (i.e., the gene is exogenous to the recombinant microorganism). The gene may be introduced into the cell by being inserted in a vector. Then, the gene in the cell may be expressed inside the vector and produce a LA transporter. In some embodiments, the gene in the cell may be expressed by being inserted in a host chromosome.

The gene that encodes a LA transporter may be heterologous (originating from a different species than the recombinant microorganism) or homologous (originating from the same species as the recombinant microorganism). Introduction of the exogenous gene in the microorganism results in higher expression of the LA transporter relative to the corresponding parent organism.

The gene that encodes a LA transporter may be a Jen1 gene or an Ady1 gene.

The Jen1 gene may comprise, consist essentially of, and consisting of the nucleotide sequence of SEQ ID NO: 2. Alternatively, a nucleotide sequence of the Jen1 gene may have more than 80%, 85%, 90%, 95%, or 99% sequence identity with the nucleotide sequence of SEQ ID NO: 2.

The Ady1 gene may comprise, consist essentially of, and consisting of the nucleotide sequence of SEQ ID NO: 4. Alternatively, a nucleotide sequence of the Ady1 gene may have more than 80%, 85%, 90%, 95%, or 99% sequence identity with the nucleotide sequence of SEQ ID NO: 4.

The gene that encodes the LA transporter may be operably connected with a promoter that may express a LA transporter. The promoter may be a constitutionally activated promoter (i.e., the promoter may be always activated) or an inducible promoter (i.e., the promoter may be activated by an inducer). Here, the inducer may be isopropryl-1-thio-β-D-galactopyranoside (IPTG).

The above-described recombinant microorganism that produces LA may be one selected from the group consisting of *Saccharomyces*, *Bacillus*, *Lactobacillus*, *Lactococcus*, *Streptococcus*, and *Kluyveromyces*. In a particular embodiment, the recombinant microorganism may be *Saccharomyces cerevisiae*.

According to another aspect of the present inventive concept, the recombinant microorganism that highly expresses a LA transporter also has little or no activity of an enzyme involved in LA degradation due to disruption of the gene encoding the enzyme.

The enzyme involved in LA degradation may convert LA into other substances. For example, the enzyme may convert LA into pyruvate, or may convert pyruvate into acetaldehyde or oxaloacetate.

The enzyme involved in LA degradation may convert LA into pyruvate. The enzyme may be lactate oxidoreductase, which is L-(+)-lactate-cytochrome c oxidoreductase (CYB2) (referred to as cytochrome b2).

The enzyme involved in LA degradation may be lactate dehydrogenase (LDH). LDH may be inhibited by a substitution in, a partial or a total deletion of, an addition to, or an insertion in a gene that encodes LDH. In one embodiment, the activity of the LDH may be inhibited by substituting the LDH gene in the microorganism with a gene that has no activity of LA degradation. The activity of the LDH gene may be also inhibited by inserting a nucleic acid in the LDH gene, wherein the nucleic acid may be an antibiotic resistance gene.

The CYB2 gene that has no activity of LA degradation may comprise, consist essentially of, and consist of the nucleotide sequence of SEQ ID NO: 5.

Activity of pyruvate decarboxylase also may be inhibited in the recombinant microorganism. A gene that encodes pyruvate decarboxylase may be a pyruvate decarboxylase 1 (pdc1) gene. Activity of the pyruvate decarboxylase may be inhibited by a substitution in, a partial or a total deletion of, an addition to, or an insertion in the pdc1 gene. In one embodiment, the activity of the pyruvate decarboxylase may be inhibited by substituting the pyruvate decarboxylase in a microorganism with a gene that has no pyruvate decarbonization activity. The activity of the pyruvate decarboxylase may be also inhibited by inserting a nucleic acid in the pdc 1 gene, wherein the nucleic acid may be an antibiotic resistance gene.

According to another aspect of the present inventive concept, a recombinant microorganism that highly expresses a LA transporter, has inhibitory activity of an enzyme involved in LA degradation, and highly expresses lactate dehydrogenase (LDH) relative to the corresponding parent microorganism is provided.

The LDH may comprise, consist essentially of, and consist of the amino acid sequence of SEQ ID NO: 6. Also, a gene encoding the LDH may comprise, consist essentially of, and consist of the nucleotide sequence of SEQ ID NO: 7.

According to another aspect of the present inventive concept, a method of producing LA using recombinant microorganisms having improved lactate production is provided.

In some embodiments, the method includes culturing a recombinant microorganism that produces LA, wherein the recombinant microorganism highly expresses a LA transporter relative to the corresponding parent microorganism.

In some other embodiments, the method includes culturing a recombinant microorganism that not only highly expresses a LA transporter, but also little or no activity of an enzyme involved in LA degradation relative to the corresponding parent microorganism.

In some other embodiments, the method includes culturing a recombinant microorganism that highly expresses a LA transporter, has inhibitory activity of an enzyme involved in LA degradation, and highly expresses LDH relative to the corresponding parent microorganism.

In order to obtain LA from the recombinant microorganism, culturing conditions may be appropriately adjusted. For example, the recombinant microorganism may be cultured under aerobic conditions for microbial growth. Thereafter, the recombinant microorganism may be cultured under anaerobic conditions to produce LA, wherein the anaerobic conditions may include a concentration of dissolved oxygen (DO) in a range from about 0 to 10%. Percent saturation is the amount of oxygen in a liter of water relative to the total amount of oxygen that the water can hold at that temperature.

The term "culturing conditions" used herein refers to conditions provided for culturing microorganisms. For example, the culturing conditions may be in regard to carbon or nitrogen sources, or oxygen conditions available to the microorganisms. The carbon source may be monosaccharides, disaccharides, or polysaccharides. In greater detail, examples of the carbon source are glucose, fructose, mannose, galactose, and the like. The nitrogen source may be an organic nitrogen compound or an inorganic nitrogen compound. In greater detail, examples of the nitrogen source are amino acids, amides, amines, nitrate, ammonium salt, and the like. The oxygen conditions may be an aerobic condition in normal oxygen partial pressure, a hypoxic condition having oxygen in a range from about 0.1 to about 10% in the air, or an oxygen-free anaerobic condition. A metabolic pathway may be adjusted according to the carbon or nitrogen source that microorganisms may actually use.

Reference will now be made in detail to embodiments, examples of which are illustrated in the accompanying drawings, wherein like reference numerals refer to like elements throughout. In this regard, the present embodiments may have different forms and should not be construed as being limited to the descriptions set forth herein. Accordingly, the embodiments are merely described below, by referring to the figures, to explain aspects of the present description.

EXAMPLE 1

Preparation of Strains that Over-Express Lactic Acid (LA) Transporters

In order to over-express LA transporters, a Jen1 gene (SEQ ID NO: 2) and an Ady2 gene (SEQ ID NO: 4) were selected, and then a vector (i.e., pRS426GP-D-Jen1 or pRS426GPD-Ady2) that is able to be expressed in *S. cerevisiae* was prepared. Examples of recombinant strains are *S. cerevisiae* (SP1001 (KCTC12310BP), SP1002 (KCTC12311BP), or SP1003 (KCTC12312BP) where lactate dehydrogenase was introduced for LA production. Each of the above strains were deposited with the Korean Collection for Type Cultures, Korea Research Institute of Bioscience and Biotechnology, Republic of Korea, on Nov. 15, 2012. The genotypes of *S. cerevisiae* strains used herein are as follows:

TABLE 1

| Strain | Description |
| --- | --- |
| SP1001 | Δpdc1::LDH |
| SP1002 | Δpdc1::LDH Δcyb2 |

EXAMPLE 2

Preparation of Strains that Over-Express LA Transporters and Lactate Dehydrogenase (LDH)

In order to determine improvement efficiency of LA production according to additional introduction of LDH genes, a strain was prepared, wherein the Cyb2 gene was removed and the LDH gene (SEQ ID No: 7) was simultaneously inserted. As in Example 1, a LA transporter over-expression vector (pRS426GPD-Jen1, pRS426GPD-Ady2) was introduced, and LA production was measured.

TABLE 2

| Strain | Description |
| --- | --- |
| SP1003 | Δpdc1::LDH Δcyb2::LDH |

EXAMPLE 3

Measurement of LA Production Using Strains that Over-Express LA Transporters and have Inhibitory Pathway of LA Degradation In order to determine improvement efficiency of LA production according to a strain over-expressing LA transporters and having an inhibitory pathway of LA degradation pathway, a LA transporter over-expression vector (pRS426GPD-Jen1, pRS426GPD-Ady2) was introduced into a strain that has the Cyb2 gene removed. LA production was measured using the strain prepared according to Example 1.

TABLE 3

LA production effect of strains that over-express LA transporters and have inhibitory pathway of LA degradation.

| Strain | Over-expression | LA production (g/L) | Production efficiency |
| --- | --- | --- | --- |
| SP1001 | Jen1 | 4.66 | 1.15 |
| | Ady2 | 5.14 | 1.27 |
| | Control | 4.05 | 1 |
| SP1002 | Jen1 | 8.53 | 2.11 |
| | Ady2 | 9.29 | 2.29 |
| | Control | 8.08 | 2.00 |

When Ady2 transporters were over-expressed, the SP1001 strain showed improvement on LA production of 1.09 g/L compared to a control group (see SP1001 Control (empty) and Table 1). Also, the SP1002 strain showed improvement on LA production of 1.21 g/L compared to a control group (see SP1002 Control (empty) and Table 1).

When the LA degradation pathway was inhibited, LA production was significantly increased. For example, in the SP1002 strain wherein Cyb2 activity is inhibited by disruption of the Cyb2 gene, LA production was significantly increased compared to a control group (see SP1002 Control and Table 1).

With regard to over-expressed Jen1, LA production in the SP1001 strain was 4.66 g/L while that in the SP1002 strain was 8.53 g/L. That is, when enzymatic activity of Cyb2 was inhibited (in the SP1002 strain), LA production was increased more than 83% relative to a strain with non-inhibited Cyb2 activity (the SP1001 strain).

With regard to over-expressed Ady2, LA production in the SP1001 strain was 5.14 g/L while that in the SP1002 strain was 9.29 g/L. That is, when enzymatic activity of Cyb2 is inhibited (in the SP1002 strain), LA production was increased more than 80% relative to a strain with non-inhibited Cyb2 activity (the SP1001 strain).

In addition, when the LA degradation pathway was inhibited, or when LA transporters were over-expressed, LA production was increased. With regard to the over-expressed Jen1, LA production was increased more than 5% relative to the corresponding strain that does not over-express Jen1. With regard to the over-expressed Ady2, LA production was increased more than 15% relative to the corresponding strain that does not over-express Ady2.

As a result, when the transporters were over-expressed and the degradation pathway was inhibited at the same time, LA production was increased 110% (i.e., SP1002, Jen1) with regard to the over-expression of Jen1 compared to a control group (i.e., SP1001, Control), and LA production was increased 129% (i.e., SP1002, Ady2) with regard to the over-expression of Ady2 compared to a control group (i.e., SP1001, Control).

EXAMPLE 4

Improvement of LA Production According to the Additional Introduction of LDH Genes Efficiency of LA production according to the additional introduction of LDH genes was confirmed using microorganisms prepared according to Examples 1 and 2.

TABLE 4

Improvement effect of LA production according to additional introduction of LDH genes

| Strain | Over-expression | LA production (g/L) | Production efficiency |
|---|---|---|---|
| SP1002 (Δpdc1::LDH Δcyb2) | Jen1 | 8.53 | 1 |
| | Ady2 | 9.29 | 1 |
| SP1003 (Δpdc1::LDH Δcyb2::LDH) | Jen1 | 13.2 | 1.55 |
| | Ady2 | 13.3 | 1.43 |

SP1003 strain compared to the. With regard to the over-expressed Jen1 gene, LA production was increased 55% in the SP1003 relative to the SP1002 strain. With regard to the over-expressed Ady2 gene, LA production was increased 43% in the SP1003 relative to the SP1002 strain.

[Industrial Applicability]

In order to reduce LA production cost, efficiency of LA production needs to be increased. When LA is produced using microorganisms, LA production cost may be reduced and become industrially applicable. However, the microorganisms only produce lactic acid at a certain concentration, and thus, the recombinant microorganisms with increased production efficiencies may be industrially applicable. In greater detail, the recombinant microorganisms according to some embodiments of the present inventive concept increase LA production, and thus the recombinant microorganism and a method of LA production using the same may be industrially applicable.

As described above, according to the one or more of the above embodiments of the present inventive concept, efficiency of the LA production may be improved using a recombinant microorganism over-expressing a LA transporter gene, wherein lactate degradation is inhibited. Also, an additional introduction of an LDH gene may increase efficiency of the LA production.

It should be understood that the exemplary embodiments described herein should be considered in a descriptive sense only and not for purposes of limitation. Descriptions of features or aspects within each embodiment should typically be considered as available for other similar features or aspects in other embodiments.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all pos- sible variations thereof is encompassed by the invention unless otherwise indicated herein or otherwise clearly contradicted by context.

What is claimed is:

1. A recombinant microorganism comprising a lactic acid (LA) transporter, wherein the expression of the LA transporter in the recombinant microorganism is increased relative to a parent microorganism;
   wherein activity of lactate oxidase in the recombinant microorganism is inhibited relative to the parent microorganism by disruption of a gene encoding L-(+)-lactate-cytochrome c oxidoreductase (cyb2) in the recombinant microorganism;
   wherein the LA transporter is Ady2,
   wherein activity of pyruvate decarboxylase (pdc) in the recombinant microorganism is inhibited relative to the parent microorganism,
   wherein expression of lactate dehydrogenase (LDH) in the recombinant microorganism is increased relative to the parent microorganism, and
   wherein the recombinant microorganism is *Saccharomyces*.

2. The recombinant microorganism of claim 1, wherein a lactic acid transporter gene is introduced into the recombinant microorganism.

3. The recombinant microorganism of claim 1, wherein lactic acid transporter comprises an amino acid sequence having at least 95% sequence identity to SEQ ID NO: 3.

4. The recombinant microorganism of claim 1, wherein the cyb2 gene comprises the nucleotide sequence of SEQ ID NO: 5.

5. The recombinant microorganism of claim 1, wherein the inhibitory activity of the lactate oxidase is caused by a substitution in, a partial or a total deletion of, an addition of, or an insertion of a nucleotide in the gene that encodes cyb2.

6. The recombinant microorganism of claim 1, wherein the pyruvate decarboxylase activity is inhibited by disruption of a gene encoding the pyruvate decarboxylase in the recombinant microorganism, wherein the gene is pyruvate decarboxylase 1 (pdc1).

7. The recombinant microorganism of claim 1, wherein the lactate dehydrogenase comprises the amino acid sequence of SEQ ID No: 6.

8. A method of producing lactic acid, the method comprising culturing the recombinant microorganism of claim 1, thereby producing lactic acid.

9. The method of claim 8, wherein the culturing is performed under anaerobic conditions.

10. The method of claim 9, wherein the anaerobic conditions have a dissolved oxygen concentration in a range from about 0 to about 10%.

11. The recombinant microorganism of claim 1, wherein the recombinant microorganism includes at least 2 copies of the nucleotide sequence encoding the lactate dehydrogenase.

* * * * *